United States Patent
Takahashi et al.

(10) Patent No.: US 10,267,789 B2
(45) Date of Patent: Apr. 23, 2019

(54) METHOD OF REDUCING INTERFERENCE FROM COMPONENT OUTSIDE OF MEASUREMENT SYSTEM

(75) Inventors: Hiroshi Takahashi, Ryugasaki (JP); Yuki Takahashi, Ryugasaki (JP); Kazunori Saito, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 13/638,469

(22) PCT Filed: Mar. 31, 2011

(86) PCT No.: PCT/JP2011/058356
§ 371 (c)(1),
(2), (4) Date: Nov. 6, 2012

(87) PCT Pub. No.: WO2011/125912
PCT Pub. Date: Oct. 13, 2011

(65) Prior Publication Data
US 2013/0052658 A1 Feb. 28, 2013

(30) Foreign Application Priority Data
Mar. 31, 2010 (JP) .................................. 2010-081678

(51) Int. Cl.
G01N 33/537 (2006.01)
G01N 33/543 (2006.01)

(52) U.S. Cl.
CPC ... *G01N 33/5375* (2013.01); *G01N 33/54313* (2013.01)

(58) Field of Classification Search
CPC ...................... G01N 33/54313; G01N 33/5375
See application file for complete search history.

(56) References Cited

U.S. PATENT DOCUMENTS

| | | | |
|---|---|---|---|
| 4,536,478 A * | 8/1985 | Sokoloff et al. | 436/533 |
| 4,921,787 A * | 5/1990 | Riggin | G01N 33/56988 435/5 |
| 5,486,479 A | 1/1996 | Ito et al. | |
| 5,710,006 A * | 1/1998 | Kiaei et al. | 435/6.12 |
| 5,888,824 A * | 3/1999 | Isogawa et al. | 436/18 |
| 5,906,744 A * | 5/1999 | Carroll | B01L 3/5082 210/516 |
| 6,777,246 B2 * | 8/2004 | Lawrence et al. | 436/533 |
| 2004/0091940 A1* | 5/2004 | Sawai et al. | 435/7.1 |
| 2007/0249062 A1* | 10/2007 | Kageyama | 436/514 |

FOREIGN PATENT DOCUMENTS

| | | | |
|---|---|---|---|
| EP | 0679892 A1 | 11/1995 | |
| EP | 1970704 A1 * | 9/2008 | ....... G01N 33/54313 |
| EP | 2508885 A1 | 10/2012 | |
| JP | 07-198721 A | 8/1995 | |
| JP | 7-301632 A | 11/1995 | |
| JP | 09-068529 A | 3/1997 | |
| JP | 09-107994 A | 4/1997 | |
| JP | 11-014628 A | 1/1999 | |

OTHER PUBLICATIONS

English translation of International Preliminary Report on Patentability and Written Opinion dated Nov. 22, 2012, in PCT International Application No. PCT/JP2011/058356.
International Search Report for PCT/JP2011/058356 dated May 10, 2011.
Ujie et al., "Interference of Agent for Coating Blood Collection Tubes with Latex Immunoaggulutination Reaction", The Japanese Journal of Medical Technology, vol. 49, No. 10, pp. 1399-1403, 2000.
Extended European Search Report for Application No. 11765812.0 dated Jul. 17, 2013.
Uchiyama et al., "Latex Gyoshuho o Mochiita Myoglobin Sokutei ni Okeru Saiketsukan no Eikyo", Okayama Eisei Kensa, vol. 40, No. 2, pp. 6-10 and 22, 2003.

* cited by examiner

*Primary Examiner* — Andrea S Grossman
(74) *Attorney, Agent, or Firm* — Birch, Stewart, Kolasch & Birch, LLP

(57) ABSTRACT

An object of the present invention is to provide a method of reducing interference to a measurement system from water-soluble silicone and/or surfactant contaminating the measurement system in a latex agglutination immunoassay. The execution of a latex immunoagglutination reaction in the presence of a silicone compound can reduce the interference to the measurement system from a component derived from a micro blood-collection tube (water-soluble silicone) and/or surfactant mixed from outside of the measurement system.

10 Claims, No Drawings

METHOD OF REDUCING INTERFERENCE FROM COMPONENT OUTSIDE OF MEASUREMENT SYSTEM

TECHNICAL FIELD

The present invention relates to i) a method of reducing interference to a measurement system from a component outside of the measurement system and water-soluble silicone and/or surfactant contaminating the measurement system in particular, characterized in that a latex immunoagglutination reaction is performed in the presence of a silicone compound in a latex agglutination immunoassay (latex immunoagglutination assay) using latex particles supporting a substance having a high affinity for the analyte or supporting the analyte, ii) a reagent used in the method of reducing the interference, and iii) the latex agglutination immunoassay with the interference reduced.

BACKGROUND ART

A latex immunoagglutination assay (latex turbidimetric immunoagglutination method) (hereinafter also referred to as an LTIA method) is frequently used in the field of clinical examination as a measurement (assay) method of an analyte (hereinafter also referred to as a target component) in a biological sample. The LTIA method is a measurement method using, for example, latex particles supporting an antibody to a target component (hereinafter also referred to as antibody-supporting latex particles) so as to detect a degree of agglutination (turbidity) of latex particles generated due to binding of an antigen, i.e., the target component, and the antibody-supporting latex particles, with an optical means (e.g., a turbidimetric method measuring transmitted light, a nephelometric method measuring scattering light) etc.

It is known that a surfactant-like substance interferes with immunological measurement systems including the LTIA method. The presence of a certain surfactant in an immunological measurement system may cause a problem such as inhibiting of an antigen-antibody reaction itself and dissociating of the antigen-antibody binding formed by the antigen-antibody reaction. The LTIA method is a homogeneous measurement method in which an antigen-antibody reaction is performed in one liquid phase, and results in an environment in which materials making up a measurement system such as the antibody-supporting latex particles are continually exposed to surfactant during measurement and, therefore, this may lead to the occurrence of interferences to the measurement system in a composite manner, such as causing a change in the structure of an analyte itself, the formation of a complex with an analyte, the nonspecific adsorption to the antibody-supporting latex particles, and the detachment of antibodies and blocking proteins supported by latex particles, due to the surfactant.

When blood is collected from a subject in the case where blood (whole blood, serum, or plasma) is used as a biological sample, preventive components (hereinafter also referred to as blood collection tube-processing agents) may have been applied to the inner wall and the cap of a blood collection tube so as to prevent blood (blood clot) from sticking to the inner wall of the blood collection tube and bubbling in the blood collection tube and the cap portion and to prevent insufficient coagulation for acquiring serum and insufficient separation of serum layer and blood cell layer. A certain kind of silicone compound is used by itself as a blood collection tube-processing agent and is used as a medium for applying other blood collection tube-processing agent than silicone compounds to the inner wall and the cap in some cases.

Some reports have been made for the interference to the LTIA method from a component applied to the inner wall of a blood collection tube. Non-Patent Literature 1 reports that a reduction in measurement value is observed when a measurement sample acquired with a commercially available micro blood collection tube is measured with the LTIA method. Non-Patent Literature 1 points out water-soluble silicone released from the inner wall of the blood collection tube as a causative substance and describes measurement results in which measurement samples with water-soluble silicone added were measured with a plurality of LTIA reagents. In Non-Patent Literature 1, consideration is also given to the interference when surfactants (BRIJ®35, TWEEN®20, TRITON® X-100) were added to measurement samples and it is reported that the reduction in measurement value was observed as was the case with water-soluble silicone. Non-Patent Literature 2 reports that measurement samples acquired with a plurality of blood collection tubes were measured with a plurality of LTIA reagents and that the reduction in measurement value was observed when a measurement sample acquired with a micro blood collection tube was measured as was the case with Non-Patent Literature 1, and water-soluble silicone released from the inner wall of the blood collection tube is also pointed out as a causative substance in this case.

A micro blood collection tube is often used when blood is collected from newborns having a smaller body weight as compared to adults. Even if the micro blood collection tube is used, a predetermined amount of blood cannot easily be collected in some cases, resulting in collected blood less than the predetermined amount. In such a case, a concentration of the blood collection tube-processing agent is increased in the measurement sample and the interference to the measurement system is expected to be prominent.

The surfactants considered in Non-Patent Literature 1 are used as nonspecific reaction-preventing agents and cleaning agents in immunological measurement methods including ELISA and are also frequently used in biochemical automated analyzers used in clinical assays as cleaning agents of: probes for dispensing or stirring measurement samples and reagents; flow passages of reagents; and repeatedly used reaction tanks. Thus, attention must be given to the interference due to mixing of the surfactants into a measurement system in the case of LTIA agents which are necessarily used in the automated analyzers.

Despite such a situation, no report has been made of a method of avoiding the interference from these surfactants and a method of reducing the interference from the surfactants when a measurement sample acquired through a micro blood collection tube is measured with the LTIA method in particular.

CITATION LIST

Non-Patent Literature

Non-Patent Literature 1: Japanese Journal of Medical Technology, Vol. 49, No. 10 (2000), pp. 1399-1403.
Non-Patent Literature 2: Okayama Journal of Medical Technology, Vol. 40, No. 2 (2003), pp. 6-10.

SUMMARY OF INVENTION

Technical Problem

An objective of the present invention is to provide i) a method of reducing interference to a measurement system from water-soluble silicone and/or surfactant mixed from outside of the measurement system in a latex agglutination immunoassay using latex particles supporting a substance having a high affinity for the analyte or supporting the analyte, ii) a reagent used in the method of reducing the interference, and iii) the latex agglutination immunoassay with the interference reduced.

Solution to Problem

The present inventors have attempted verification from various viewpoints and have conducted extensive research for solving the problem in the LTIA method and have totally unexpectedly found that when a latex immunoagglutination reaction is performed in the presence of polyether-modified silicone oil, which is classified as the same silicone compound as water-soluble silicone considered as a cause of interference in Non-Patent Literatures 1 and 2, the interference to a measurement system from a component that is mixed from outside of the measurement system and derived from a micro blood collection tube can be reduced. The present inventors have also unexpectedly found that when a latex immunoagglutination reaction is performed in the presence of polyether-modified silicone oil, the interference from surfactants (BRIJ® 35, TWEEN® 20, TRITON® X-100) having structures different from water-soluble silicones can also be reduced, leading to the completion of the present invention.

The present invention comprises the following.

(1) A method of reducing interference to a measurement system from water-soluble silicone and/or surfactant mixed from outside of the measurement system, wherein a latex immunoagglutination reaction is performed in the presence of a silicone compound in a latex agglutination immunoassay.

(2) The method of (1) above, wherein the silicone compound contains polyether-modified silicone oil.

(3) The method of (1) or (2) above, wherein the silicone compound is present by allowing a latex reagent solution to contain the silicone compound.

(4) The method of (1) to (3) above, wherein the process of allowing a latex reagent solution to contain the silicone compound is based on a blocking treatment.

(5) The method of (1) to (4) above, wherein the concentration of the silicone compound at the time of the latex immunoagglutination reaction is 0.0001 to 1%.

(6) A method of reducing interference from water-soluble silicone and/or surfactant mixed in a latex agglutination immunoassay comprising the steps of:

bringing i) latex particles supporting a substance having a high affinity for the analyte and ii) a silicone compound into contact with a sample including the analyte derived from living body and the mixed water-soluble silicone and/or surfactant; and measuring an agglutination reaction of the analyte and the latex particles.

(7) A latex agglutination immunoassay comprising the step of:

bringing i) latex particles supporting a substance having a high affinity for the analyte and ii) a silicone compound into contact with a sample including the analyte derived from living body.

(8) A kit for a latex agglutination immunoassay comprising:

a first reagent including a buffering agent; and
a second reagent including latex particles supporting a substance having a high affinity for the analyte, wherein at least one of the first reagent and the second reagent includes a silicone compound.

(9) A reagent for a latex agglutination immunoassay comprising:

i) a buffering agent; ii) a silicone compound; and iii) latex particles supporting a substance having a high affinity for the analyte.

Advantageous Effects of Invention

The present invention provides a method of reducing the interference to an LTIA measurement system from water-soluble silicone and/or surfactant mixed from outside of the measurement system. The present invention enables accurate measurement even if the measurement is performed with the LTIA method using a measurement sample collected through a micro blood collection tube.

DESCRIPTION OF EMBODIMENTS (Silicone Compound)

Polyether-modified silicone oil may preferably be used as a silicone compound of the present invention. Preferable polyether-modified silicone oils include a copolymer of alkyl (having one to three carbon atoms) siloxane and polyoxyalkylene (preferably having two to five carbon atoms in an alkylene group) and a copolymer of dimethylsiloxane and polyoxyalkylene is particularly preferable. Polyoxyalkylene refers to polyoxyethylene, polyoxypropylene, and a random or block polymer of polyoxyethylene and polyoxypropylene. Examples of such polyether-modified silicone oil include a compound expressed by the following general formula (I).

[Chem 1]

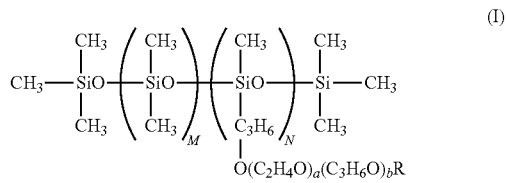

(In this formula, M, N, a, and b are average degrees of polymerization and R is hydrogen or an alkyl group)

In this case, preferably, M and N are 10 to 10,000 and 1 to 1,000, respectively, and satisfy M>N and, more preferably, M and N are 10 to 1,000 and 1 to 50, respectively, and satisfy M>N. Preferably, a is 2 to 100 and b is 0 to 50. It is preferable that R be hydrogen or an alkyl group having one to four carbon atoms.

Specific examples of commercially available products containing the polyether-modified silicone oil used in the present invention include SILWET® FZ-2166 manufactured by Nippon Unicar Company Limited, KF-618 manufactured by Shin-Etsu Chemical, SH3749, SH7090, SF8410, SH8700 manufactured by Dow Corning Toray Silicone Co., Ltd., and TSA775, TSF4440 manufactured by GE Toshiba Silicone or Momentive Performance Materials Japan LLC., and one of these products can solely be used or two or more products can be used as a mixture. These products may be mixtures with polyalkylsiloxane or silica as in the case of TSA775.

A preparation method of an LTIA reagent using a silicone compound of the present invention will hereinafter be described by taking as an example the case of using antibody-supporting latex particles as latex particles supporting a substance having a high affinity for the analyte or supporting the analyte. Although the silicone compound of the present invention may be added to either of reagent solutions, which make up the LTIA reagent, containing or not containing the antibody-supporting latex particles, the silicone compound is preferably added to the reagent solution containing the antibody-supporting latex particles. If the silicone compound is added to a reagent solution containing the antibody-supporting latex particles, the silicone compound may be added to a reagent solution containing latex particles either before or after they support an antibody while the silicone compound is preferably added to the reagent solution containing latex particles after they support an antibody. The temperature at the time of the addition of the silicone compound of the present invention is selectable to be a suitable temperature from 1 to 65 degrees C., at which the solubility of the silicone compound of the present invention is expected to be increased, as long as the function (activity) of a supported antibody is not lost, for example.

After adding the silicone compound of the present invention to the reagent solution containing latex particles after supporting an antibody, incubation can additionally be performed at a suitable temperature between 1 to 65 degrees C. for a suitable time. As a result, it can be expected that the same effect as the blocking effect is added to the antibody-supporting latex particles. If the incubation is performed, the incubation is preferably performed at 30 to 65 degrees C. If the temperature is less than 30 degrees C., the blocking effect may not sufficiently be added and, if the temperature exceeds 65 degrees C., the antibody etc., may be denatured as protein, resulting in the loss of antibody activity. The incubation at approximately 37 degrees C. can be given as one example of preferred incubation temperature. When the incubation is performed, the time is not limited and can empirically be selected in accordance with temperature so as to acquire the expected blocking effect. In this description, such heating or incubation operations may be referred to as a blocking treatment.

The concentration of the silicone compound of the present invention may be prescribed, for example, as a concentration at the time of the latex immunoagglutination reaction. Preferable concentrations include 0.0001% to 1%, 0.0002% to 1%, 0.0004% to 1%, 0.0008% to 1%, 0.002% to 1%, 0.003% to 1%, 0.006% to 1%, 0.01% to 1%, 0.03% to 1%, 0.05% to 1%, 0.0001% to 0.5%, 0.0002% to 0.5%, 0.0004% to 0.5%, 0.0008% to 0.5%, 0.002% to 0.5%, 0.003% to 0.5%, 0.006% to 0.5%, 0.01% to 0.5%, 0.03% to 0.5%, 0.05% to 0.5%, 0.0001% to 0.2%, 0.0002% to 0.2%, 0.0004% to 0.2%, 0.0008% to 0.2%, 0.002% to 0.2%, 0.003% to 0.2%, 0.006% to 0.2%, 0.01% to 0.2%, 0.03% to 0.2%, 0.05% to 0.2%, 0.0001% to 0.1%, 0.0002% to 0.1%, 0.0004% to 0.1%, 0.0008% to 0.1%, 0.002% to 0.1%, 0.003% to 0.1%, 0.006% to 0.1%, 0.01% to 0.1%, 0.03% to 0.1%, and 0.05% to 0.1%. In general, a preferred concentration is 0.0001% to 1%, preferably 0.001% to 0.5%, and more preferably 0.01% to 0.1%. Although some commercially available silicone compound products are distributed as mixtures with other components (e.g., polyalkylsiloxane and silica), concentrations (dosage of individual products) for acquiring the effect of the present invention may empirically be confirmed by reference to a method described in the examples.

As described above, the silicone compound of the present invention may be selected from a group of silicone compounds (silicone products) having an ability to reduce the interference to a measurement system from water-soluble silicone and/or surfactant mixed from outside of the measurement system in the LTIA method with consideration given to the availability of the measurement sensitivity, measurement range, and reproducibility desired for the measurement system or the stability of reagent, and thus, practically optimum type, concentration, and LTIA reagent preparation method may be utilized as needed. In this description, "reduce (reducing) the interference" means that the reduction in measurement value due to water-soluble silicone and/or surfactant is suppressed.

Although the details of water-soluble silicones used for micro blood collection tubes are not clear, commercially available water-soluble silicones include KS-538 (Shin-Etsu Silicone), KM-70 (Shin-Etsu Silicone), KM-72F (Shin-Etsu Silicone), TSA770 (Comentative), TSA732 (Comentative), TSA7341 (Comentative), AntifoamSl (Wako Pure Chemical Industries), SM5571 (Toray silicone), etc. Whether these water-soluble silicones actually cause the interference to the measurement system of the latex agglutination immunoassay can be examined by performing experiments as needed and if confirmed as an interfering component, the water-soluble silicone can be used as a material for screening a silicone compound of the present invention.

Although description above has been made by taking as an example the case of using the antibody-supporting latex particles as the latex particles supporting a substance having a high affinity for the analyte or supporting the analyte, the case of using an antigen as a supported substance must obviously be understood in the same way. From the viewpoint of a high-affinity-binding substance, the analyte is the high-affinity-binding substance. If a target component other than antigen or antibody binds to latex particles supporting a binding partner specific to the target component, and thus, agglutination of the latex particles is formed depending on the abundance of the target component, such reaction is also included in the latex immunoagglutination reaction according to the present invention.

(Latex Particles)

Although the latex particles in the present invention refer to polystyrene latex particles etc., when the latex particles are included in the latex immunoagglutination reaction described above and when a method of supporting a bonding partner specific to the target component is based on a physical process, such as hydrophobic bonding, the latex particles of the present invention include metal colloid, silica, carbon, etc. The size of the latex particles may be selected as needed from the range of 0.05 to 1 µm so as to acquire desired measurement sensitivity, measurement range, etc., in consideration of an optical measurement method used (e.g., a turbidimetric method measuring transmitted light, a nephelometric method measuring scattering light). An average particle diameter used in an optical measurement in automated analyzers is generally 0.1 to 0.4 µm and preferably 0.1 to 0.2 µm. An average particle diameter of the latex particles can be checked by a particle size analyzer, transmission electron microscope imaging, or other methods. The concentration of the latex particles in reagent solution can be selected as needed in accordance with the particle diameter of the latex particles used and the overall design of the measurement system from a range of 0.0001 mg/mL to 10 mg/mL, for example.

(Configuration Etc., as LTIA Reagent)

In addition to the main components for the reaction, the LTIA reagent (reagent solution) of the present invention may contain a component for buffering and adjusting the pH, ionic strength, osmotic pressure, etc., of the sample, such as acetic acid, citric acid, phosphoric acid, tris, glycine, boric acid, carbonic acid, and Good's buffer as well as sodium salts, potassium salts, and calcium salts thereof. The LTIA reagent may further contain a component for enhancing agglutination, such as macromolecules including polyethyleneglycol, polyvinylpyrrolidone, and phospholipid polymers. The LTIA reagent may also contain one or more of components for controlling agglutination, such as proteins, amino acids, saccharide, metal salts, surfactants, reducing agents, and chaotropic agents that are generally used for this purpose. Any components that tend to cause foaming may also be added to the assay reagents of the present invention.

Although the type of the sample to be measured (assayed) with the LTIA reagent of the present invention may be any one of a variety of biological samples, an analyte contained in the blood collected through a micro blood collection tube is preferred. The analyte (i.e. the substance of interest) can be protein, peptide, amino acid, lipid, carbohydrate, nucleic acid, or hapten, for example, or any other molecules that are quantifiable in theory. Examples of the analytes include CRP (C-reactive protein), Lp(a), MMP3 (matrix metalloproteinase 3), anti-CCP (cyclic citrullinated peptide) antibody, anti-phospholipid antibody, RPR, type IV collagen, PSA, BNP (brain natriuretic peptide), NT-proBNP, insulin, microalbumin, cystatin C, RF (rheumatoid factor), CA-RF, KL-6, PIVKA-II, FDP, D-dimer, SF (soluble fibrin), TAT (thrombin-antithrombin III complex), PIC, PAI, factor XIII, pepsinogen I/II, phenytoin, phenobarbital, carbamazepine, valproic acid, theophylline, and others.

The LTIA reagent of the present invention is made up of one or more reagent solutions, i.e., a plurality of reagent solutions, as described above. Examples of a plurality of reagent solutions include a reagent solution consisting of a buffer solution intended to adjust an analyte to a concentration preferred for measurement or to adjust an environment of the antigen-antibody reaction, a reagent solution containing antibody-supporting latex particles, etc. The silicone compound of the present invention may be contained in all of the constituent reagent solutions making up the reagent, or may be contained in any of selected constituent reagent solutions making up the assay reagent.

EXAMPLES

Although the present invention will hereinafter be described in detail by referring to the examples below, the present invention is not limited to the following examples.

[Example 1] Verification of Effect of Silicone Compound of the Present Invention (1)

Verified was the effect of the silicone compound of the present invention in measuring a sample processed with a micro blood collection tube.
<Test Method>
(1) Conventional LTIA Reagent
SS TYPE PURE AUTO®S, CRP Latex (manufactured by Sekisui Medical Co., Ltd.) was used.
(2) Test Reagent
(2-1) First Reagent
Buffer Solution 1 (2-amino-2-hydroxymethyl-1,3-propanediol buffer solution (pH 8.5) 20 mmol/L) of said conventional LTIA reagent was directly used.
(2-2) Second Reagent
(i) Control Reagent Solution
Latex Reagent Solution 2 (antihuman C-reactive protein murine monoclonal antibody-sensitized latex 2.25 mg/ml) of said conventional LTIA reagent was directly used.
(ii) Reagent Solutions of Examples 1a to 1c FZ-2166 (manufactured by Nippon Unicar Company Limited), KF-618 (manufactured by Shin-Etsu Silicone), SH3749, SH7090, SF8410, SH8700 (manufactured by Dow Corning Toray Co., Ltd.), and TSA775, TSF4440 (manufactured by GE Toshiba Silicone) were added as silicone compounds to the Control Reagent Solution at final concentrations of 0.01%, 0.03%, and 0.10% and were used after heating at 37 degrees C. for 24 hours.

(3) Preparation of Micro Blood Collection Tube-Processed Sample and Control Sample Micro blood-collection tube: A predetermined amount, i.e., 0.6 mL, or 1/12 of the predetermined amount, i.e., 0.05 mL, of whole blood was dispensed to BD MICROTAINER® MICROGUARD™ tube (catalog number: 365985; with Lithium Heparin and plasma separator additive; manufactured by Becton, Dickinson and Company, Japan; fill volume: 0.4 to 0.6 mL) and was allowed to stand still for 30 minutes after inversion to prepare a micro blood collection tube-processed sample (hereinafter respectively referred to as a 0.6-mL sample and a 0.05-mL sample). A control sample was prepared by using VENOJECT® II (code number: VP-HL050K; Lithium Heparin; manufactured by Terumo; fill volume: 5 mL).

(4) Assay Method

The four types of the second reagents (one Control Reagent Solution and three Reagent Solutions of Examples 1a to 1c) were combined with the first reagent (Buffer Solution 1 of the conventional LTIA reagent above) and used as test reagents, and the measurement samples (the control sample and the micro blood collection tube-processed samples (the 0.6-mL sample and the 0.05-mL sample)) were measured by using HITACHI 7170 Automated Analyzer (manufactured by Hitachi High-Technologies Corporation) with the following measurement parameters of (5).

(5) Measurement Parameters of HITACHI 7170 Automated Analyzer
(i) Liquid volumes: Measurement Sample, 3 µL; First Reagent, 150 µL; Second Reagent, 50 µL.
(ii) Analysis method: two-point end method (photometric point 19-34)
(iii) Measurement wavelength: 570 nm/secondary-wavelength 800 nm
(iv) Calibration: spline
(v) Calibrator: TYPE PURE AUTO® (registered trademark) S, CRP Latex, Calibrator
<Assay Result>

The absorbance of the 0.6-mL sample and the 0.05-mL sample measured by using the four types of the second reagents (one Control Reagent Solution and three Reagent Solutions of Examples 1a to 1c) is divided by the absorbance of the control sample measured by using the Control Reagent Solution as the second reagent to obtain relative absorbance (%). The result is shown in Table 1.

When the Control Reagent Solution not containing the silicone compound of the present invention was used as the second reagent to measure the micro blood collection tube-processed sample (Comparison Example 1), the reduction in relative absorbance was confirmed. Particularly for the 0.05-mL sample (acquired by dispensing 0.05 mL, which is 1/12 of the predetermined amount), it was confirmed that the relative absorbance was considerably varied (reduced) to 75.6%.

In contrast, when the Reagent Solutions of Examples 1a to 1c (containing eight types of the silicone compounds of the present invention each at three concentrations) were used as the second reagent to measure the micro blood collection tube-processed sample (Examples 1a to 1c), a slight or little variation in relative absorbance was recognized even if the 0.05-mL sample was measured.

TABLE 1

| | Comp. Example 1 0.00% | | Example 1a 0.01% | | Example 1b 0.03% | | Example 1c 0.10% | |
|---|---|---|---|---|---|---|---|---|
| | Micro Blood Collection Tube-Processed Sample | | | | | | | |
| Silicone Compound | 0.6 mL | 0.05 mL | 0.6 mL | 0.05 mL | 0.6 mL | 0.05 mL | 0.6 mL | 0.05 mL |
| None (Con. Re. Sol.) | 92.7 | 75.6 | | | | | | |
| FZ-2166 | | | 98.9 | 101.8 | 98.8 | 99.7 | 99.9 | 101.1 |
| KF-618 | | | 99.8 | 95.0 | 97.7 | 98.8 | 100.9 | 102.0 |
| SH3749 | | | 98.4 | 96.8 | 100.8 | 98.3 | 100.1 | 100.2 |
| SH7090 | | | 99.6 | 95.4 | 97.9 | 98.5 | 101.1 | 101.2 |
| SH8410 | | | 97.2 | 93.9 | 100.8 | 97.8 | 99.8 | 99.3 |
| SH8700 | | | 99.2 | 96.2 | 99.7 | 98.8 | 99.8 | 99.1 |
| TSA775 | | | 100.3 | 97.6 | 99.5 | 99.0 | 99.0 | 100.2 |
| TSF4440 | | | 97.6 | 95.5 | 99.7 | 98.4 | 98.9 | 98.9 |

Con. Re. Sol. = Control Reagent Solution (%)

[Example 2] Consideration of Preparation Method of LTIA Reagent Using Silicone Compound of the Present Invention Consideration was given to a preparation method of the LTIA reagent using the silicone compound of the present invention.
<Test Method>
(1) Conventional LTIA Reagent
The same conventional LTIA reagent as Example 1 was used.
(2) Test Reagent
(2-1) First Reagents
(i) Control Reagent Solution R1
Buffer Solution 1 of said conventional LTIA reagent was directly used.
(ii) Reagent Solution of Example 2a
TSA775 was added to the Control Reagent Solution R1 at final concentrations of 0.01% and 0.03% and used after heating at 37 degrees C. for 24 hours.
(2-2) Second Reagents
(i) Control Reagent Solution R2
Latex Reagent Solution 2 of said conventional LTIA reagent was directly used.
(ii) Reagent Solution of Example 2b
TSA775 was added to the Control Reagent Solution R2 at final concentrations of 0.01% and 0.03% and used after standing still at 10 degrees C. or lower for 24 hours.
(iii) Reagent Solution of Example 2c
TSA775 was added to the Control Reagent Solution R2 at final concentrations of 0.01% and 0.03% and used after heating at 37 degrees C. for 24 hours.
(3) Preparation of Micro Blood Collection Tube-Processed Sample and Control Sample
The 0.6-mL sample, the 0.05-mL sample, and the control sample were prepared as is the case with Example 1.
(4) Assay Method
The first reagents and the second reagents were used as test reagents in the following four types of combinations, and the measurement samples (the control sample and the micro blood collection tube-processed samples (the 0.6-mL sample and the 0.05-mL sample)) were measured by using HITACHI 7170 Automated Analyzer with the following measurement parameters of (5).

Comparison Example 2: Control Reagent Solution R1 and Control Reagent Solution R2

Example 2a: Reagent Solution of Example 2a and Control Reagent Solution R2

Example 2b: Control Reagent Solution R1 and Reagent Solution of Example 2b

Example 2c: Control Reagent Solution R1 and Reagent Solution of Example 2c (5) Measurement Parameters of HITACHI 7170 Automated Analyzer
The conditions were the same as Example 1.
<Assay Result>
The measurement values (values acquired through concentration conversion by the calibrator) of the 0.6-mL sample and the 0.05-mL sample measured by using the four combinations of the first and second reagents (Comparison Example 2 and Examples 2a to 2c) are divided by the measurement value of the control sample measured by using the combination of the first and second reagents of Comparison Example 2 to obtain relative measurement values (%). The result is shown in Table 2.
When the micro blood collection tube-processed sample was measured with the combination of the Control Reagent Solution R1 and the Control Reagent Solution R2 containing no silicone compound of the present invention (Comparison Example 2), the reduction in relative measurement value was confirmed.
In contrast, when the micro blood collection tube-processed sample was measured by using the Reagent Solutions of Examples 2a to 2c containing the silicone compound of the present invention (Examples 2a to 2c), a slight or little variation in relative measurement value was recognized even if the 0.05-mL sample was measured.
In Examples 2a to 2c using the reagent solutions containing the silicone compound of the present invention, the average values of relative measurement values (four types) of the 0.6-mL sample and the 0.05-mL sample at two silicone compound concentrations were 96.0% (Example 2a), 98.3% (Example 2b), and 100.5% (Example 2c). From the results above, the highest interference reducing effect was acquired among the three examined conditions when the silicone compound of the present invention was added to the reagents containing the antibody-supporting latex and heated at 37 degrees C. for 24 hours.

It was considered that this may be attributed to the improvement in the solubility of the silicone compound in the reagent solutions or the addition of the same effect as the blocking effect due to the heating and incubation.

TABLE 2

| First Reagent | Comp. Example 2 Con. Re. Sol. R2 | Example 2a Con. Re. Sol. R2 Added to First Reagent | | Example 2b Con. Re. Sol. R1 Example 2b Added to Second Reagent and allowed to stand still at 10 degrees C or lower | | Example 2c Con. Re. Sol. R1 Example 2c Added to Second Reagent and heated at 37 degrees C for 24 hours | |
|---|---|---|---|---|---|---|---|
| Silicone Compound Sol. R2 | | 0.01% | 0.03% | 0.01% | 0.03% | 0.01% | 0.03% |
| 0.6 mL | 92.7 | 96.9 | 96.7 | 98.8 | 100.4 | 101.1 | 96.8 |
| 0.05 mL | 77.0 | 93.4 | 96.8 | 93.3 | 100.7 | 102.7 | 101.2 |

Con. Re. Sol. = Control Reagent Solution (%)

[Example 3] Verification of Effect of Silicone Compound of the Present Invention (2)

The effect of the silicone compound of the present invention in measurement of a surfactant-added sample was verified.

<Test Method>

(1) Conventional LTIA Reagent

The same conventional LTIA reagent as Example 1 was used.

(2) Test Reagent (2-1) First Reagent

Buffer Solution 1 of the conventional LTIA reagent was directly used.

(2-2) Second Reagent (i) Control Reagent Solution

Latex Reagent Solution 2 of the conventional LTIA reagent was directly used.

(ii) Reagent Solution of Example 3

TSA775 was added to the Control Reagent Solution at a final concentration of 0.01% and used after heating at 37 degrees C. for 20 hours.

(3) Preparation of Surfactant-Added Sample and Control Sample

TRITON® X-100 (polyoxyethylene (10) octylphenylether), TWEEN® 20 (polyoxyethylene sorbitan monolaurate), and BRIJ® 35 (polyoxyethylene (23) lauryl ether) were added to serum acquired by dispensing whole blood into a glass test tube at additive concentrations (final concentrations) described in Table 3 to prepare the surfactant-added samples. Serum with saline was used as the control sample.

(4) Assay Method

The two types of the second reagents (the Control Reagent Solution and the Reagent Solution of Example 3) were combined with the first reagent (Buffer Solution 1 of the conventional LTIA reagent) and used as test reagents, and the measurement samples (the control sample and the surfactant-added samples) were measured by using HITACHI 7170 Automated Analyzer with the following measurement parameters of (5).

(5) Measurement Parameters of HITACHI 7170 Automated Analyzer

The conditions were the same as Example 1.

<Assay Result>

The measurement values (values acquired through concentration conversion by the calibrator) of the surfactant-added samples measured by using the two combinations of the first and second reagents (Comparison Example 3 and Example 3) are divided by the measurement value of the control sample measured by using the combination of the first and second reagents of Comparison Example 3 to obtain relative measurement values (%). The result is shown in Table 3.

In Example 3 where the silicone compound of the present invention is contained, a fluctuation range of the relative measurement values was smaller as compared to Comparison Example 3. Particularly in the case of higher surfactant concentrations, the difference became significant.

It was also found out that the LTIA measurement system using the method of the present invention can avoid the interference of the surfactants described in Non-Patent Literature 1.

TABLE 3

| Surfactant | Additive Conc. | Comp. Ex. 3 | Example 3 |
|---|---|---|---|
| TritonX-100 | 0.10% | 91.4 | 100.0 |
| | 1.00% | 0.0 | 54.3 |
| Tween20 | 0.10% | 92.9 | 95.2 |
| | 0.50% | 66.7 | 83.3 |
| Brij35 | 0.10% | 97.6 | 97.6 |
| | 1.00% | 88.1 | 95.2 |
| | | | (%) |

INDUSTRIAL APPLICABILITY

The present invention provides a method of reducing interference to an LTIA measurement system from water-soluble silicone and/or surfactant mixed from outside of the measurement system. The present invention enables accurate measurement even if a measurement sample collected through a micro blood-collection tube is used for performing measurement with the LTIA method.

The invention claimed is:

1. A method of suppressing reduction in measurement value of an analyte in a biological sample in a homogeneous latex agglutination immunoassay and obtaining a measurement value of an analyte comprising the steps of:

combining a polyether-modified silicone oil and a reagent solution containing antibodies physically bound to latex particles, wherein the antibodies are antibodies to the analyte in the biological sample, and thereby obtaining a mixture, incubating the mixture at a temperature between 1 and 65 degrees C., providing the biological sample in a blood collection tube, wherein a water-soluble silicone which reduces the measurement value of the analyte, a surfactant which reduces the measurement value of the analyte, or both have been applied to an inner wall or a cap of said blood collection tube, adding the biological sample in the blood collection tube to the mixture after the incubation of the mixture, suppressing reduction in measurement value of the analyte in the homogeneous latex agglutination immunoassay, and detecting agglutination of the latex particles by optically measuring absorbance of the mixture, and thereby, obtaining the measurement value of the analyte,
wherein the polyether-modified silicone oil comprises the compound of formula (I):

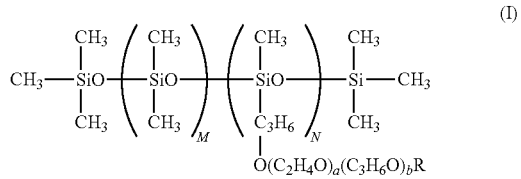

wherein M is 10-10,000 and N is 1 to 1,000, and M>N, a is 2 to 100 and b is 0 to 50, and R is hydrogen or an alkyl group having one to four carbon atoms.

2. The method of claim 1, wherein a concentration of the polyether-modified silicone oil at the time of performing the latex agglutination immunoassay is 0.0001 to 1%.

3. The method of claim 1, wherein said antibodies are physically bound to the latex particles by hydrophobic bonding.

4. The method of claim 1, wherein said temperature is a temperature between 30 and 65 degrees C.

5. The method of claim 1, wherein said surfactant is a surfactant selected from the group consisting of polyoxyethylene (23) lauryl ether, polyoxyethylene sorbitan monolaurate, and octoxinol.

6. A homogeneous latex agglutination immunoassay for obtaining a measurement value of an analyte in a biological sample comprising the step of:
combining a polyether-modified silicone oil and a reagent solution containing antibodies physically bound to latex particles, wherein the antibodies are antibodies to the analyte in the biological sample, and thereby obtaining a mixture,
incubating the mixture at a temperature between 1 and 65 degrees C.,
providing the biological sample in a blood collection tube, wherein a water-soluble silicone which reduces the measurement value of the analyte, a surfactant which reduces the measurement value of the analyte, or both have been applied to an inner wall or a cap of said blood collection tube,
adding the biological sample in the blood collection tube to the mixture after the incubation of the mixture, and
detecting agglutination of the latex particles by optically measuring absorbance of the mixture, and thereby, obtaining the measurement value of the analyte;
wherein the polyether-modified silicone oil comprises the compound of formula (I):

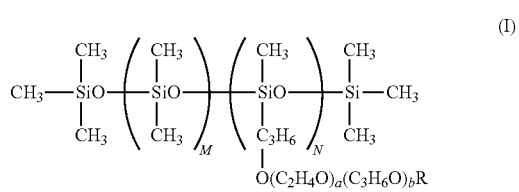

wherein M is 10-10,000 and N is 1 to 1,000, and M>N, a is 2 to 100 and b is 0 to 50, and R is hydrogen or an alkyl group having one to four carbon atoms.

7. The method of claim 6, wherein a concentration of the polyether-modified silicone oil at the time of performing the latex agglutination immunoassay is 0.0001 to 1%.

8. The method of claim 6, wherein said antibodies are physically bound to the latex particles by hydrophobic bonding.

9. The method of claim 6, wherein said temperature is a temperature between 30 and 65 degrees C.

10. The method of claim 6, wherein said surfactant is a surfactant selected from the group consisting of polyoxyethylene (23) lauryl ether, polyoxyethylene sorbitan monolaurate, and octoxinol.

* * * * *